United States Patent
Ho et al.

(10) Patent No.: US 11,913,047 B2
(45) Date of Patent: Feb. 27, 2024

(54) METHOD FOR PRODUCING γ-AMINOBUTYRIC ACID AND FERMENTED CULTURE PREPARED THEREBY

(71) Applicant: GLAC BIOTECH CO., LTD., Tainan (TW)

(72) Inventors: Hsieh-Hsun Ho, Tainan (TW); Ching-Wei Chen, Tainan (TW); Yu-Fen Huang, Tainan (TW); Chen-Hung Hsu, Tainan (TW); Wen-Yang Lin, Tainan (TW); Yi-Wei Kuo, Tainan (TW); Shin-Yu Tsai, Tainan (TW)

(73) Assignee: GLAC BIOTECH CO., LTD., Tainan (TW)

(*) Notice: Subject to any disclaimer, the term of this patent is extended or adjusted under 35 U.S.C. 154(b) by 169 days.

(21) Appl. No.: 17/647,436

(22) Filed: Jan. 7, 2022

(65) Prior Publication Data
US 2022/0315960 A1    Oct. 6, 2022

(30) Foreign Application Priority Data

Mar. 31, 2021 (TW) .................................. 110111908
Aug. 30, 2021 (TW) .................................. 110132130

(51) Int. Cl.
*C12P 13/00* (2006.01)
*C12N 1/20* (2006.01)
(Continued)

(52) U.S. Cl.
CPC .......... *C12P 13/001* (2013.01); *A23L 33/135* (2016.08); *C12N 1/205* (2021.05); *C12P 39/00* (2013.01);
(Continued)

(58) Field of Classification Search
CPC ....... C12P 13/001; C12P 39/00; C12P 13/005; A23L 33/135; C12N 1/205;
(Continued)

(56) References Cited

U.S. PATENT DOCUMENTS

| 2002/0106424 A1* | 8/2002 | Ogawa .................. | A23L 33/175 426/52 |
| 2020/0390119 A1* | 12/2020 | Hsieh .................... | A23C 19/062 |
| 2021/0401908 A1* | 12/2021 | Ho ........................ | A61K 35/745 |

FOREIGN PATENT DOCUMENTS

KR    20130076723 A  *  7/2013

OTHER PUBLICATIONS

Yunes et al., "GABA production and structure of gadB/gadC genes in Lactobacillus and Bifidobacterium strains from human microbiota", Anaerobe, vol. 42, pp. 197-204. 2016 (Year: 2016).*

(Continued)

*Primary Examiner* — Nikki H. Dees
*Assistant Examiner* — Maura E. Sweeney
(74) *Attorney, Agent, or Firm* — Hamre, Schumann, Mueller & Larson, P.C.

(57) ABSTRACT

A method for producing γ-aminobutyric acid includes cultivating, in a culture medium containing glutamic acid or a salt thereof, a probiotic composition including at least one lactic acid bacterial strain selected from the group consisting of *Bifidobacterium breve* CCFM1025 which is deposited at the Guangdong Microbial Culture Collection Center under an accession number GDMCC 60386, *Lactobacillus acidophilus* TYCA06, *Lactobacillus plantarum* LPL28, and *Bifidobacterium longum* subsp. *infantis* BLI-02 which are deposited at the China General Microbiological Culture Collection Center respectively under accession numbers CGMCC 15210, CGMCC 17954, and CGMCC 15212, *Lactobacillus salivarius* subsp. salicinius AP-32 which is deposited at the China Center for Type Culture Collection (Continued)

under an accession number CCTCC M 2011127, and combinations thereof.

14 Claims, 3 Drawing Sheets

(51) Int. Cl.
    *C12P 39/00*     (2006.01)
    *A23L 33/135*     (2016.01)
    *C12R 1/23*     (2006.01)
    *C12R 1/25*     (2006.01)

(52) U.S. Cl.
    CPC ..... *A23V 2002/00* (2013.01); *A23V 2400/113* (2023.08); *A23V 2400/169* (2023.08); *A23V 2400/181* (2023.08); *A23V 2400/519* (2023.08); *A23V 2400/529* (2023.08); *C12R 2001/23* (2021.05); *C12R 2001/25* (2021.05)

(58) Field of Classification Search
    CPC .......... A23V 2002/00; A23V 2400/169; A23V 2400/181; A23V 2400/529; C12R 2001/23; C12R 2001/25; C12R 2001/01; C12R 2001/225
    See application file for complete search history.

(56) References Cited

OTHER PUBLICATIONS

Diez-Gutierrez et al., "Gamma-aminobutyric acid and probiotics: Multiple health benefits and their future in global functional food and nutraceuticals market", Journal of Functional Foods, vol. 64, Jan. 2020 (Year: 2020).*

* cited by examiner

METHOD FOR PRODUCING γ-AMINOBUTYRIC ACID AND FERMENTED CULTURE PREPARED THEREBY

CROSS-REFERENCE TO RELATED APPLICATION

This application claims priority of Taiwanese Invention Patent Application Nos. 110111908 and 110132130, filed on Mar. 31, 2021 and Aug. 30, 2021, respectively.

FIELD

The present disclosure relates to a method for producing γ-aminobutyric acid and a fermented culture prepared by the method.

BACKGROUND

γ-Aminobutyric acid (GABA) is an inhibitory neurotransmitter found in microorganisms and plants, and in the mammalian central nervous system and peripheral tissues. GABA is primarily synthesized from glutamic acids or glutamate salts via a decarboxylation reaction that is catalyzed by glutamate decarboxylase (GAD).

GABA has been found to exert various effects on the human body, such as enhancing immunity, promoting blood circulation, lowering blood pressure, stabilizing blood sugar, relieving stress, inhibiting anxiety, etc., and is useful for alleviating various disorders such as sequelae of stroke, hypertension, depression, insomnia, menopausal syndrome, irritable bowel syndrome (IBS), etc. Since GABA exerts beneficial pharmacological effects, researchers in the pharmaceutical and/or biotechnology industry endeavor to develop methods for mass production of GABA so as to meet the high market demand. In this regard, microbial fermentation has advantages such as low cost, fast production rate, high safety, etc., and hence, is widely applied for producing GABA.

Lactic acid bacteria (LAB) are gram-positive, lactic acid-producing bacteria that are conferred with the generally recognized as safe (GRAS) status, and are widely used as probiotics, which are considered as "live microbial food ingredient" with beneficial effects on human health. LAB have been reported to selectively stimulate the growth of native bacteria in the gastrointestinal tract, change the composition, quantity and nature of the intestinal microflora, and promote the host's gastrointestinal health, thereby enhancing the host's immune response. Examples of common LAB include *Lactobacillus* spp., *Lactococcus* spp., *Pediococcus* spp., *Streptococcus* spp., *Enterococcus* spp., *Bifidobacterium* spp., *Bacillus* spp., *Leuconostoc* spp., etc.

Previous studies have reported that certain strains of *Lactobacillus* spp. and *Bifidobacterium* spp. are capable of producing GABA. As reviewed in Cui Y. et al., (2020), *Int. J. Mol. Sci.*, 21(3): 995, examples of *Lactobacillus* spp. with a GABA-producing capability include *L. brevis* 877G, *L. brevis* CGMCC 1306, *L. buchneri* OPM-1, *L. delbrueckii* subsp. *bulgaricus* PR1, *L. fermentum* YS2, *L. paracasei* NFRI 7415, *L. plantarum* ATCC 14917, etc.

In spite of the aforesaid report, due to the high demand for GABA in the market, there is still a need to develop a new strategy that can be utilized for mass production of GABA.

SUMMARY

Therefore, in a first aspect, the present disclosure provides a method for producing γ-aminobutyric acid (GABA) which can alleviate at least one of the drawbacks of the prior art.

The method includes cultivating a probiotic composition including at least one lactic acid bacterial strain capable of producing GABA in a culture medium containing glutamic acid or a salt thereof. The at least one lactic acid bacterial strain is selected from the group consisting of *Bifidobacterium breve* CCFM1025 which is deposited at the Guangdong Microbial Culture Collection Center (GDMCC) under an accession number GDMCC 60386, *Lactobacillus acidophilus* TYCA06 which is deposited at the China General Microbiological Culture Collection Center (CGMCC) under an accession number CGMCC 15210, *Lactobacillus plantarum* LPL28 which is deposited at the CGMCC under an accession number CGMCC 17954, *Bifidobacterium longum* subsp. *infantis* BLI-02 which is deposited at the CGMCC under an accession number CGMCC 15212, *Lactobacillus salivarius* subsp. *salicinius* AP-32 which is deposited at the China Center for Type Culture Collection (CCTCC) under an accession number CCTCC M 2011127, and combinations thereof.

In a second aspect, the present disclosure provides a fermented culture including GABA, which can alleviate at least one of the drawbacks of the prior art, and which is prepared by the aforesaid method.

In a third aspect, the present disclosure provides a pharmaceutical composition, which can alleviate at least one of the drawbacks of the prior art, and which includes the aforesaid fermented culture and optionally a pharmaceutically acceptable carrier.

In a fourth aspect, the present disclosure provides a food product, which can alleviate at least one of the drawbacks of the prior art, and which includes the aforesaid fermented culture.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

In the development of methods for enhancing the production of γ-aminobutyric acid (GABA), the applicant surprisingly found that certain lactic acid bacterial strains not only have an excellent capability to produce GABA in large amounts, but also exhibit a synergistic effect when used in combination. Hence these strains are expected to enhance the overall production (i.e., mass production) of GABA.

Therefore, the present disclosure provides a method for producing GABA, which includes cultivating a probiotic composition including at least one lactic acid bacterial strain capable of producing GABA in a culture medium containing glutamic acid or a salt thereof.

The at least one lactic acid bacterial strain is selected from the group consisting of *Bifidobacterium breve* CCFM1025 which is deposited at the Guangdong Microbial Culture Collection Center (GDMCC) under an accession number GDMCC 60386, *Lactobacillus acidophilus* TYCA06 which is deposited at the China General Microbiological Culture Collection Center (CGMCC) under an accession number CGMCC 15210, *Lactobacillus plantarum* LPL28 which is deposited at the CGMCC under an accession number CGMCC 17954, *Bifidobacterium longum* subsp. *infantis* BLI-02 which is deposited at the CGMCC under an accession number CGMCC 15212, *Lactobacillus salivarius* subsp. *salicinius* AP-32 which is deposited at the China Center for Type Culture Collection (CCTCC) under an accession number CCTCC M 2011127, and combinations thereof.

According to the present disclosure, the culture medium may be prepared by adding glutamic acid or a salt thereof to a basal medium suitable for growing a lactic acid bacterial strain.

In certain embodiments, the culture medium may include one of L-glutamic acid and monosodium glutamate (MSG), or a combination thereof.

In certain embodiments, the monosodium glutamate may be added to the basal medium in an amount ranging from 1 wt % to 5 wt % based on the total weight of the culture medium. In other embodiments, the monosodium glutamate may be added to the basal medium in an amount ranging from 1 wt % to 3 wt % based on the total weight of the culture medium. In an exemplary embodiment, the monosodium glutamate is added to the basal medium in an amount of 3 wt % based on the total weight of the culture medium.

According to the present disclosure, the basal medium may be purchased commercially or self-prepared using standard techniques well known to those skilled in the art. Examples of the basal medium may include, but are not limited to, MRS (De Man, Rogosa and Sharpe) broth and MRS broth supplemented with cysteine.

According to the present disclosure, the basal medium may include a carbon source selected from the group consisting of glucose, fructose, lactose, sucrose, maltose, galactose, mannose, trehalose, starch, potato starch, malt extract, maltodextrin, and combinations thereof.

In certain embodiments, the basal medium may include 1 wt % to 15 wt % of glucose based on the total weight of the basal medium. In other embodiments, the basal medium may include 1 wt % to 5 wt % of glucose based on the total weight of the basal medium. In an exemplary embodiment, the basal medium includes 5 wt % of glucose based on the total weight of the basal medium.

According to the present disclosure, the basal medium may include a nitrogen source selected from the group consisting of ammonium sulfate [$(NH_4)_2SO_4$], ammonium phosphate [$(NH_4)_3PO_4$], ammonium nitrate ($NH_4NO_3$), ammonium chloride ($NH_4Cl$), casamino acid, peptone, polypeptone, tryptone, meat extract, yeast extract, yeast powder, milk, skimmed milk powder, soybean flour, whey, and combinations thereof.

In certain embodiments, the basal medium may include, based on the total weight of the basal medium, 0 wt % to 25 wt % of skimmed milk powder, 0 wt % to 15 wt % of peptone, and 1 wt % to 15 wt % of yeast extract. In other embodiments, the basal medium may include, based on the total weight of the basal medium, 2 wt % to 15 wt % of skimmed milk powder, 3 wt % to 10 wt % of peptone, and 1 wt % to 5 wt % of yeast extract. In an exemplary embodiment, the basal medium includes, based on the total weight of the basal medium, 12 wt % of skimmed milk powder, 7 wt % of peptone, and 3% wt % of yeast extract.

As used herein, the term "cultivating" can be used interchangeably with other terms such as "fermentation" and "culturing".

It should be noted that the procedures and operating conditions for cultivating the lactic acid bacterial strain may be adjusted according to practical requirements. In this regard, those skilled in the art may refer to journal articles, e.g., Hsieh P.S. et al. (2013), *New Microbiol.*, 36:167-179.

According to the present disclosure, the cultivation of the lactic acid bacterial strain may be performed at a temperature ranging from 25° C. to 40° C. In an exemplary embodiment, the cultivation of the lactic acid bacterial strain is performed at a temperature of 37° C.

According to the present disclosure, the cultivation of the lactic acid bacterial strain may be performed for a time period ranging from 20 hours to 40 hours. In an exemplary embodiment, the cultivation of the lactic acid bacterial strain is performed for a time period of 24 hours.

According to the present disclosure, the probiotic composition may include three lactic acid bacterial strains that are selected from the group consisting of the aforesaid *Bifidobacterium breve* CCFM1025, *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32.

In certain embodiments, the probiotic composition may include any one of the following bacterial combinations: a combination of *Bifidobacterium breve* CCFM1025, *Lactobacillus acidophilus* TYCA06, and *Lactobacillus plantarum* LPL28; a combination of *Bifidobacterium breve* CCFM1025, *Lactobacillus acidophilus* TYCA06, and *Lactobacillus salivarius* subsp. *salicinius* AP-32; a combination of *Bifidobacterium breve* CCFM1025, *Bifidobacterium longum* subsp. *infantis* BLI-02, and *Lactobacillus salivarius* subsp. *salicinius* AP-32; a combination of *Lactobacillus plantarum* LPL28, *Bifidobacterium longum* subsp. *infantis* BLI-02, and *Lactobacillus salivarius* subsp. *salicinius* AP-32; a combination of *Lactobacillus acidophilus* TYCA06, *Lactobacillus plantarum* LPL28, and *Bifidobacterium longum* subsp. *infantis* BLI-02; a combination of *Bifidobacterium breve* CCFM1025, *Lactobacillus acidophilus* TYCA06, and *Bifidobacterium longum* subsp. *infantis* BLI-02; a combination of *Bifidobacterium breve* CCFM1025, *Lactobacillus plantarum* LPL28, and *Lactobacillus salivarius* subsp. *salicinius* AP-32; a combination of

*Lactobacillus acidophilus* TYCA06, *Bifidobacterium longum* subsp. *infantis* BLI-02, and *Lactobacillus salivarius* subsp. *salicinius* AP-32; a combination of *Bifidobacterium breve* CCFM1025, *Lactobacillus plantarum* LPL28, and *Bifidobacterium longum* subsp. *infantis* BLI-02; and a combination of *Lactobacillus acidophilus* TYCA06, *Lactobacillus plantarum* LPL28, and *Lactobacillus salivarius* subsp. *salicinius* AP-32.

In an exemplary embodiment, the probiotic composition includes *Lactobacillus acidophilus* TYCA06, *Lactobacillus plantarum* LPL28, and *Bifidobacterium breve* CCFM1025.

According to the present disclosure, a ratio of a number of *Lactobacillus acidophilus* TYCA06 to that of *Lactobacillus plantarum* LPL28 and to that of *Bifidobacterium breve* CCFM1025 ranges from 1:0.2:0.2 to 1:5:1. In an exemplary embodiment, the ratio of the number of *Lactobacillus acidophilus* TYCA06 to that of *Lactobacillus plantarum* LPL28 and to that of *Bifidobacterium breve* CCFM1025 is 1:4:2.

According to the present disclosure, the probiotic composition may include four lactic acid bacterial strains that are selected from the group consisting of the aforesaid *Bifidobacterium breve* CCFM1025, *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32.

In certain embodiments, the probiotic composition may include any one of the following bacterial combinations: a combination of *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32; a combination of *Bifidobacterium breve* CCFM1025, *Lactobacillus plantarum* LPL28, *Bifidobacterium longum* subsp. *infantis* BLI-02, and *Lactobacillus salivarius* subsp. *salicinius* AP-32; a combination of *Bifidobacterium breve* CCFM1025, *Lactobacillus acidophilus* TYCA06, *Bifidobacterium longum* subsp. *infantis* BLI-02, and *Lactobacillus salivarius* subsp. *salicinius* AP-32; a combination of *Bifidobacterium breve* CCFM1025, *Lactobacillus acidophilus* TYCA06, *Lactobacillus plantarum* LPL28, and *Lactobacillus salivarius* subsp. *salicinius* AP-32; and a combination of *Bifidobacterium breve* CCFM1025, *Lactobacillus acidophilus* TYCA06, *Lactobacillus plantarum* LPL28, and *Bifidobacterium longum* subsp. *infantis* BLI-02.

In an exemplary embodiment, the probiotic composition includes *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32.

According to the present disclosure, a ratio of a number of *Lactobacillus acidophilus* TYCA06 to that of *Lactobacillus plantarum* LPL28, to that of *Bifidobacterium longum* subsp. *infantis* BLI-02, and to that of *Lactobacillus salivarius* subsp. *salicinius* AP-32 ranges from 1:0.067:0.067:0.067 to 1:4:4:4. In an exemplary embodiment, the ratio of the number of *Lactobacillus acidophilus* TYCA06 to that of *Lactobacillus plantarum* LPL28, to that of *Bifidobacterium longum* subsp. *infantis* BLI-02, and to that of *Lactobacillus salivarius* subsp. *salicinius* AP-32 is 1:1:1:1.

The present disclosure also provides a fermented culture including GABA, which is prepared by the abovementioned method.

Based on the known pharmacological activity of GABA, the fermented culture of the present disclosure is expected to be capable of improving immunity, treating disorders, such as insomnia, depression, and hypertension, ameliorating sleep disorders, anxiety, menopausal syndromes, and gastrointestinal tract disorders, etc.

Therefore, the present disclosure also provides a pharmaceutical composition including the aforesaid fermented culture and optionally a pharmaceutically acceptable carrier.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

According to the present disclosure, the pharmaceutical composition may be made into a dosage form suitable for oral administration or topical administration using technology well-known to those skilled in the art.

Examples of the dosage form for oral administration include, but are not limited to, sterile powders, tablets, troches, lozenges, pellets, capsules, dispersible powders or granules, solutions, suspensions, emulsions, drops, syrup, elixirs, slurry, and the like.

Examples of the dosage form for topical administration to the skin (i.e., manufactured as an external preparation) include, but are not limited to, emulsions, gels, ointments, creams, patches, liniments, powders, aerosols, sprays, lotions, serums, pastes, foams, drops, suspensions, salves, and bandages.

Moreover, the present disclosure provides a food product including the aforesaid fermented culture. The food product may be prepared using a standard technique well known to one of ordinary skill in the art. For example, the fermented culture may be directly added to an edible material as a food additive, or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, milk powders, beverages, confectionery, candies, fermented foods, animal feeds, health foods, dietary supplements, jelly, infant formulas, dressings, mayonnaise, spreads, creams, sauces, puddings, ice cream, and ketchup.

The present disclosure will be further described by way of the following examples. However, it should be understood that the following examples are intended solely for the purpose of illustration and should not be construed as limiting the present disclosure in practice.

EXAMPLES

General Experimental Materials

1. Culture medium

The culture medium used in the following examples included a glutamate salt (i.e., monosodium glutamate (MSG)) and was prepared using the recipe shown in Table 1 below.

TABLE 1

| Ingredients | Source | Amount (wt %) |
| --- | --- | --- |
| Glucose | Union Chemical Co., Ltd. | 1-5 |
| Skimmed milk | Warrnambool Cheese & | 2-15 |

TABLE 1-continued

| Ingredients | Source | Amount (wt %) |
|---|---|---|
| powder | Butter Factory Company Holdings Ltd. | |
| Peptone | STBIO MEDIA, Inc. | 3-10 |
| Yeast extract | Angel Yeast Co., Ltd. | 1-5 |
| Potassium hydrogen phosphate | Budenheim USA, Inc. | 0.05-0.2 |
| Sodium citrate | Qingdao Fuso Refining & Processing Co., Ltd. | 0-0.1 |
| Manganese (II) sulfate (MnSO$_4$) | Jost Chemical Co. | 0-0.1 |
| MSG | PT Cheil Jedang Indonesia | 1-5 |
| Tween 80 | Musim Mas Holdings | 0.05-0.2 |

The balance is deionized water.

2. Lactic acid bacterial (LAB) strains

A. *Bifidobacterium breve* CCFM1025

*Bifidobacterium breve* CCFM1025, which is disclosed in Chinese Invention Patent No. CN 108949640 B and is known and readily available to the public, and which was originally deposited at the Guangdong Microbial Culture Collection Center (GDMCC) of Guangdong Institute of Microbiology (No. 59 Building, No. 100 Xianliezhong Road, Guangzhou 510075, China) under an accession number GDMCC 60386 on Jun. 11, 2018 by the researchers from Jiangnan University, China, and which has also been deposited at the Bioresource Collection and Research Center (BCRC) of the Food Industry Research and Development Institute (FIRDI) (No. 331, Shih-Pin Rd., Hsinchu City 300, Taiwan) under an accession number BCRC 911057 since May 7, 2021, after the applicant was granted authorization to access by the original depositor (i.e., the researchers from Jiangnan University).

B. *Lactobacillus acidophilus* TYCA06

*Lactobacillus acidophilus* TYCA06, which is disclosed in the applicant's Taiwanese Invention Patent No. TW 1709374 B and is known and readily available to the public, has been deposited at the BCRC of the FIRDI under an accession number BCRC 910813 since Jan. 18, 2018, and has also been deposited at the China General Microbiological Culture Collection Center (CGMCC) of Chinese Academy of Sciences, the Institute of Microbiology (No. 1, West Beichen Rd., Chacyang District, Beijing 100101, China), under an accession number CGMCC 15210 since Jan. 15, 2018.

C. *Lactobacillus plantarum* LPL28

*Lactobacillus plantarum* LPL28, which is disclosed in the applicant's Taiwanese Invention Patent No. TW 1739495 B, has been deposited at the BCRC of the FIRDI under an accession number BCRC 910536 since Dec. 27, 2011, and has also been deposited at the CGMCC of Chinese Academy of Sciences, the Institute of Microbiology, under an accession number CGMCC 17954 since Jun. 18, 2019.

D. *Bifidobacterium longum* subsp. *infantis* BLI-02

*Bifidobacterium longum* subsp. *infantis* BLI-02, which is disclosed in TW 1739495 B, has been deposited at the BCRC of the FIRDI under an accession number BCRC 910812 since Jan. 18, 2018, and has also been deposited at the CGMCC of Chinese Academy of Sciences, the institute of Microbiology, under an accession number CGMCC 15212 since Jan. 15, 2018.

E. *Lactobacillus salivarius* subsp. *salicinius* AP-32

*Lactobacillus salivarius* subsp. *salicinius* AP-32, which is disclosed in TW 1709374 B and is known and readily available to the public, has been deposited at the BCRC of the FIRDI under an accession number BCRC 910437 since Jul. 30, 2009, and has also been deposited at the China Center for Type Culture Collection (CCTCC) of Wuhan University, the College of Life Sciences (No. 299, Bayi Rd., Wuchang District, Wuhan City 430072, Hubei Province, China) under an accession number CCTCC 2011127 since Apr. 10, 2011.

F. Comparative LAB strains

The applicant isolated the following LAB strains for them to serve as comparative bacterial strains: *Bifidobacterium breve* gL-57 which was isolated from the breast milk of a healthy subject and has substantially similar morphology and characteristics as those of *Bifidobacterium breve* CCFM1025, *Lactobacillus acidophilus* gL-6 which was isolated from the feces of a healthy subject and has similar morphology and characteristics as those of *Lactobacillus acidophilus* TYCA06, *Lactobacillus plantarum* gL-335 which was isolated from the feces of a healthy subject and has similar morphology and characteristics as those of *Lactobacillus plantarum* LPL28, *Bifidobacterium longum* subsp. *infantis* gL-54 which was isolated from the feces of a healthy subject and has similar morphology and characteristics as those of *Bifidobacterium longum* subsp. *infantis* BLI-02, and *Lactobacillus salivarius* subsp. *salicinius* gL-301 which was isolated from the feces of a healthy subject and has similar morphology and characteristics as those of *Lactobacillus salivarius* subsp. *salicinius* AP-32. Identification of these comparative bacterial strains was verified using analytical profile index (API) test and 16S ribosomal DNA analysis according to procedures known to those skilled in the art (data not shown).

GENERAL PROCEDURES

1. Determination of γ-aminobutyric Acid (GABA) Concentration

In the following experiments, each test sample was subjected to amino acid derivatization using AccQ-Tag Chemistry Kit (Manufacturer: Waters Corporation; Catalogue No.: WAT052875) according to the manufacturer's instruction, and then to high performance liquid chromatography (HPLC) analysis using Alliance e2695 XE HPLC system (Manufacturer: Waters Corporation) and Altus™ A-10 HPLC Fluorescence UV detector (Manufacturer: PerkinElmer, Inc.), so as to determine the GABA concentration therein. The operating parameters and conditions for performing HPLC are summarized in Table 2 below. In comparison, an amino acid standard H (Manufacturer: Waters Corporation; Catalogue No.: WAT088122) added with GABA (Manufacturer: Sigma-Aldrich; Catalogue No.: 03835), serving as a control standard, was also subjected to the aforesaid amino acid derivatization and HPLC analysis so as to prepare a standard curve.

TABLE 2

| | |
|---|---|
| Type of chromatography column | AccQ-Taq Amino Acid Analysis Nova-Pak ® C18 Column (Manufacturer: Waters Corporation; Catalogue No.: WAT052885) |
| Size of chromatography column | Length: 150 mm; inner diameter: 3.9 mm |
| Temperature of chromatography column | 25° C. |
| Injection volume | 10 μL |

TABLE 2-continued

| | |
|---|---|
| Type of chromatography column | AccQ-Taq Amino Acid Analysis Nova-Pak® C18 Column (Manufacturer: Waters Corporation; Catalogue No.: WAT052885) |
| Detection wavelength of test sample | 274 nm |
| Mobile phase | Gradient elution: ddH$_2$O/an aqueous solution (10%, v/v) of AccQ-Tag Eluent A (Catalogue No.: WAT052890)/acetonitrile |
| Flow rate of test sample | 1.0 mL/min |

2. Statistical Analysis

All the experiments described below were performed in triplicates. The experimental data of all the test groups are expressed as mean±standard deviation (SD), and were analyzed using two-tailed Student's t-test using GraphPad Prism 5 software (Developer: GraphPad Sofware, Inc., San Diego, CA), so as to assess the differences between the groups. Statistical significance is indicated by p<0.05.

EXAMPLE 1. EVALUATION OF THE EFFECT OF LACTIC ACID BACTERIAL (LAB) STRAINS ON PRODUCTION OF GABA

In order to evaluate the efficacy of certain lactic acid bacterial strains on the production of GABA, the following experiments were conducted.

A. Preparation of Fermented Culture

A respective one of the ten LAB strains described in section 2 of the General Experimental Materials was inoculated into 100 mL of a culture medium as described in section 1 of the General Experimental Materials, and was then cultured at a temperature of 37° C. for 24 hours, thereby obtaining a respective one of activated LAB inoculums having a bacterial concentration of 1×10$^9$ CFU/mL.

Next, the respective LAB inoculum was inoculated in an amount of 3% (v/v) into 5 L of a culture medium as described in section 1 of the General Experimental Materials, and was then cultured under an anaerobic condition at a temperature of 37° C. overnight to obtain an LAB fermented culture serving as a single-LAB group, i.e., a corresponding one of single-LAB experimental groups 1 to 5 (abbreviated as single-LAB EG1 to EG5) and single-LAB comparative groups 1 to 5 (abbreviated as single-LAB CG1 to CG5) shown in Table 3 below.

In addition, the LAB inoculums of *Lactobacillus acidophilus* TYCA06 and *Lactobacillus plantarum* LPL28 were mixed with that of *Bifidobacterium breve* CCFM1025 or that of *Bifidobacterium breve* gL-57 at a specified number ratio shown in Table 4. The resultant LAB inoculum mixture was subjected to anaerobic cultivation using the aforesaid procedures and conditions. The resultant fermented culture served as a three-LAB group, i.e., a corresponding one of three-LAB experimental groups 1 to 7 (abbreviated as three-LAB EG1 to EG7) and a three-LAB comparative group (abbreviated as three-LAB CG) shown in Table 4.

Moreover, the LAB inoculums of *Lactobacillus plantarum* LPL28, *Bifidobacterium longum* subsp. *infantis* BLI-02, and *Lactobacillus salivarius* subsp. *salicinius* AP-32 were mixed with that of *Lactobacillus acidophilus* TYCA06 or that of *Lactobacillus acidophilus* gL-6 at a specified number ratio shown in Table 5. The resultant LAB inoculum mixture was subjected to anaerobic cultivation using the aforesaid procedures and conditions. The resultant fermented culture served as a four-LAB group, i.e., a corresponding one of four-LAB experimental groups 1 to 9 (abbreviated as four-LAB EG1 to EG9) and a four-LAB comparative group (abbreviated as four-LAB CG) shown in Table 5.

Furthermore, a blank control group was prepared generally according to the aforesaid procedures and conditions except that the culture medium was not inoculated with any of the LAB strain.

TABLE 3

| Group | LAB strain |
|---|---|
| Single-LAB EG1 | *Bifidobacterium breve* CCFM1025 |
| Single-LAB EG2 | *Lactobacillus acidophilus* TYCA06 |
| Single-LAB EG3 | *Lactobacillus plantarum* LPL28 |
| Single-LAB EG4 | *Bifidobacterium longum* subsp. *infantis* BLI-02 |
| Single-LAB EG5 | *Lactobacillus salivarius* subsp. *salicinius* AP-32 |
| Single-LAB CG1 | *Bifidobacterium breve* gL-57 |
| Single-LAB CG2 | *Lactobacillus acidophilus* gL-6 |
| Single-LAB CG3 | *Lactobacillus plantarum* gL-335 |
| Single-LAB CG4 | *Bifidobacterium longum* subsp. *infantis* gL-54 |
| Single-LAB CG5 | *Lactobacillus salivarius* subsp. *salicinius* gL-301 |

TABLE 4

| Group | Ratio of number of *Lactobacillus acidophilus* TYCA06, *Lactobacillus plantarum* LPL28, and *Bifidobacterium breve* CCFM1025 |
|---|---|
| Three-LAB EG1 | 1:0.067:0.067 |
| Three-LAB EG2 | 1:0.2:0.2 |
| Three-LAE EG3 | 1:1:1 |
| Three-LAB EG4 | 1:1:5 |
| Three-LAB EG5 | 1:4:2 |
| Three-LAB EG6 | 1:5:1 |
| Three-LAB EG7 | 1:15:1 |
| Three-LAB CG | 1:1:1 (*Bifidobacterium breve* CCFM1025 being replaced with *Bifidobacterium breve* gL-57) |

TABLE 5

| Group | Ratio of number of *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32 |
|---|---|
| Four-LAB EG1 | 1:0.067:0.067:0.067 |
| Four-LAB EG2 | 1:0.25:0.25:0.25 |
| Four-LAB EG3 | 1:1:1:1 |
| Four-LAB EG4 | 1:1:1:4 |
| Four-LAB EG5 | 1:1:4:1 |
| Four-LAB EG6 | 1:4:1:1 |
| Four-LAB EG7 | 1:1:1:15 |
| Four-LAB EG8 | 1:1:15:1 |
| Four-LAB EG9 | 1:15:1:1 |
| Four-LAB CG | 1:1:1:1 (*Lactobacillus acidophilus* TYCA06 being replaced with *Lactobacillus acidophilus* gL-6) |

B. Determination of GABA Concentration in Fermented Culture

The fermented culture of each group obtained in section A of this example was subjected to centrifugation at 25° C. under a speed of 12,000×g for 10 minutes to form a supernatant and a pellet. After that, 10 μL of the supernatant was taken as a test sample, and was then subjected to determination of GABA concentration according to the method as described in section 1 of the General Procedures.

Furthermore, the supernatant formed by centrifuging a respective one of the fermented cultures of the single-LAB EG2 to EG5 and four-LAB EG1 was also subjected to a spray-drying treatment so as to obtain a bacterial powder. Then, the bacterial powder was dissolved in pure water to obtain a bacterial suspension, followed by subjecting the bacterial suspension to determination of GABA concentration according to the method as described in section 1 of the General Procedures.

The relative amount of GABA produced in the fermented culture of the respective group was determined as the percentage of the GABA concentration in the fermented culture of the respective group relative to the GABA concentration of the blank control group. The differences between the groups were statistically analyzed according to the procedures described in section 2 of the General Procedures.

Figure 1:
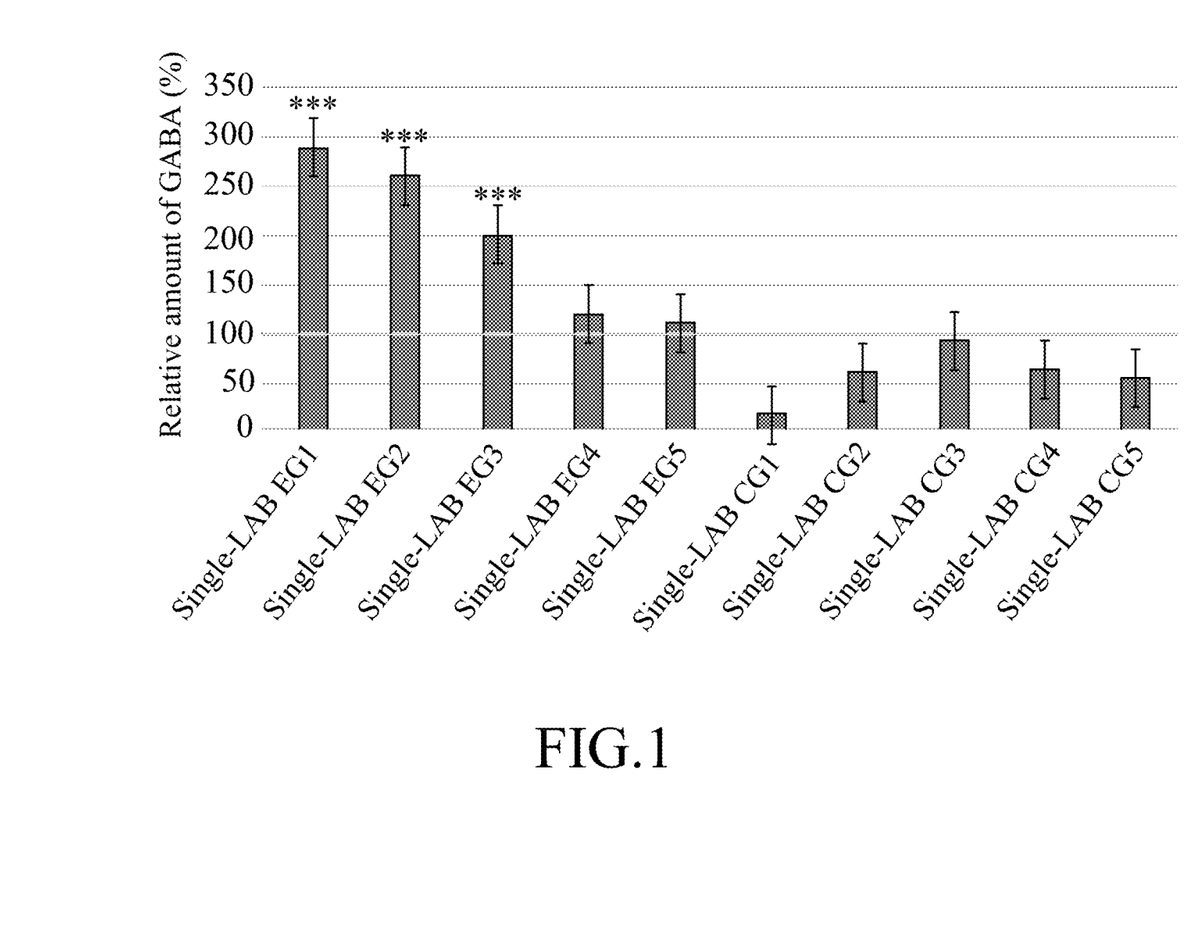
FIG. 1 shows the relative amount of γ-aminobutyric acid (GABA) in the fermented cultures of the single-LAB experimental groups 1 to 5 (EG1 to EG5) and single-LAB comparative groups 1 to 5 (CG1 to CG5) of Example 1, infra, in which the symbol "***" represents $p<0.001$ (compared with the blank control group)

FIG. 1 shows the relative amount of GABA produced in the fermented culture of each single-LAB group. As shown in FIG. 1, the relative amount of GABA produced in the fermented culture of each of the single-LAB CG1 to CG5 was less than 100%, indicating that GABA was not produced in the fermented cultures of the single-LAB CG1 to CG5. In contrast, the relative amount of GABA produced in the fermented culture of each of the single-LAB EG1 to EG5 was greater than 100%, and the relative amount of GABA produced in the fermented culture of the single-LAB EG1 was increased to almost 300%. It can be seen that *Bifidobacterium breve* CCFM1025, *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32 (in particular *Bifidobacterium breve* CCFM1025) have an excellent GABA production capability as compared with other strains of *Bifidobacterium breve*, *Lactobacillus acidophilus*, *Lactobacillus plantarum*, *Bifidobacterium longum* subsp. *infantis*, and *Lactobacillus salivarius* subsp. *salicinius*.

Figure 2:
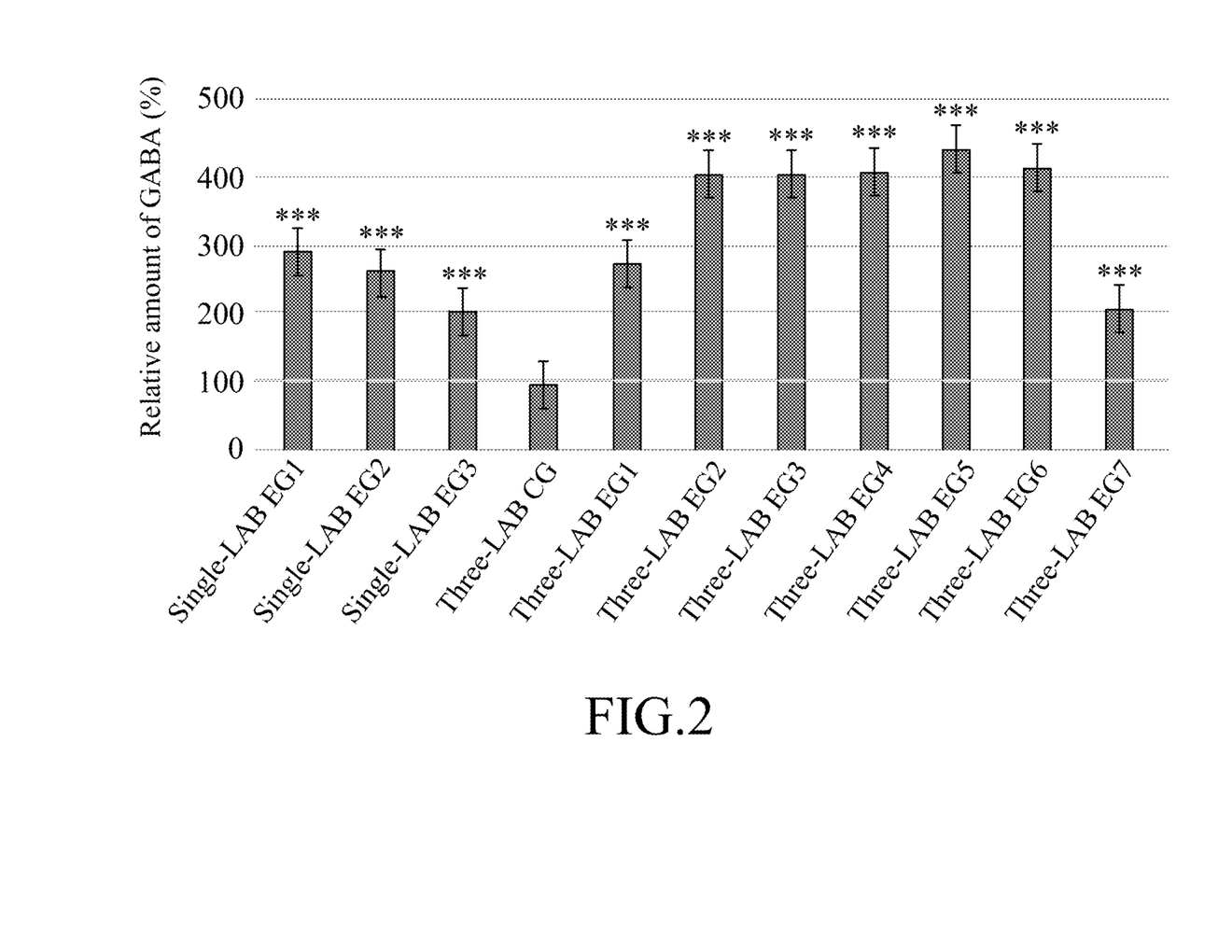
FIG. 2 shows the relative amount of GABA in the fermented cultures of the single-LAB EG1 to EG3, three-LAB CG, and three-LAB EG1 to EG7 of Example 1, infra, in which the symbol "*" represents $p<0.001$ (compared with the blank control group)

FIG. 2 shows the relative amount of GABA produced in the fermented cultures of the three-LAB groups and single-LAB EG1 to EG3. As shown in FIG. 2, the relative amount of GABA produced in the fermented culture of each of the three-LAB EG2 to EG6 was significantly higher compared with that of the single-LAB EG1 to EG3, and the relative amount of GABA produced in the fermented cultures of the three-LAB EG5 and EG6 even exceeded 400%. On the contrary, the relative amount of GABA produced in the fermented cultures of the three-LAB EG1 and EG7 was significantly lower compared with that of the three-LAB EG2 to EG6, and was even lower than that of at least one of the single-LAB EG1 and EG2. This result suggests that, *Lactobacillus acidophilus* TYCA06, *Lactobacillus plantarum* LPL28, and *Bifidobacterium breve* CCFM1025, when mixed in a specific number ratio ranging from 1:0.2:0.2 to 1:5:1, can produce a synergistic effect so as to greatly improve the overall capability of GABA production. However, when these three LAB strains are mixed in other ratios, the synergistic effect cannot be achieved, and might even adversely affect the overall GABA production capability.

In addition, the relative amount of GABA produced in the fermented culture of the three-LAB CG was not only significantly lower than that of the three-LAB EG2 to EG6, but also lower than that of the single-LAB EG1 to EG3 and three-LAB EG1 and EG7. It can be seen that replacing one of the three required LAB strains in the three-LAB group with a non-required LAB strain (e.g., *Bifidobacterium breve* CCFM1025 being replaced with *Bifidobacterium breve* gL-57 in this example) not only fails to achieve the aforesaid synergistic effect, but also results in a significant negative impact on the overall GABA production capability.

Figure 3:
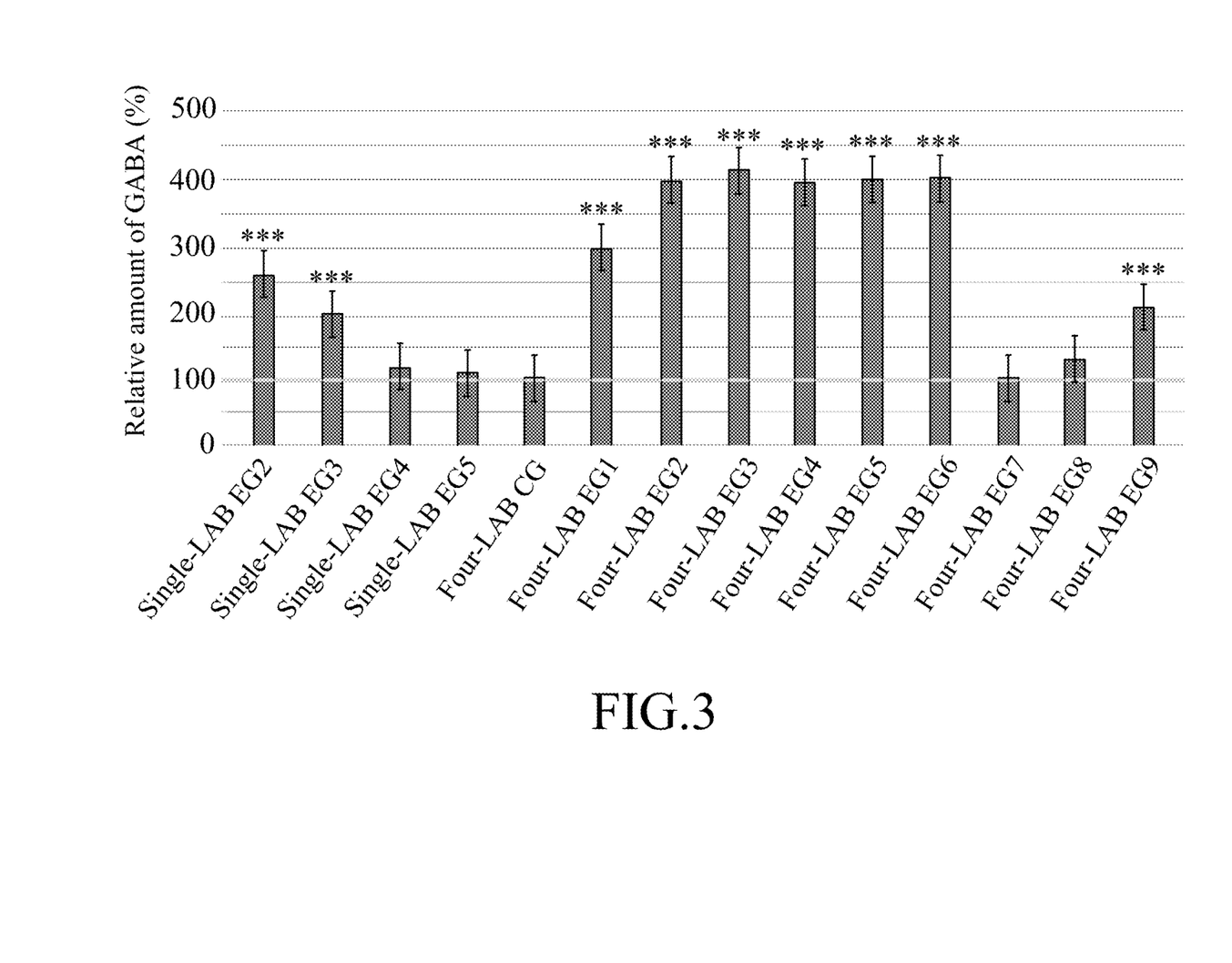
FIG. 3 shows the relative amount of GABA in the fermented cultures of the single-LAB EG2 to EG5, four-LAB CG, and four-LAB EG1 to EG9 of Example 1, infra, in which the symbol "*" represents $p<0.001$ (compared with the blank control group).

FIG. 3 shows the relative amount of GABA produced in the fermented cultures of four-LAB groups and single-LAB EG2 to EG5. As shown in FIG. 3, the relative amount of GABA produced in the fermented cultures of the four-LAB EG1 to EG6 was significantly higher compared with that of the single-LAB EG2 to EG5, and the relative amount of GABA produced in the fermented culture of the four-LAB EG3 even exceeded 400%. In contrast, the relative amount of GABA produced in the fermented cultures of the four-LAB EG7 to EG9 was significantly lower compared with that of the single-LAB EG2. This result suggests that, *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32, when mixed in a specific number ratio ranging from 1:0.067:0.067:0.067 to 1:4:4:4, can produce a synergistic effect so as to greatly improve the overall capability of GABA production. However, when these four LAB strains are mixed in other ratios, the synergistic effect cannot be seen, and might even adversely affect the overall GABA production capability.

In addition, the relative amount of GABA produced in the fermented culture of the four-LAB CG was not only significantly lower than that of the four-LAB EG1 to EG6, but also lower than that of the single-LAB EG2 to EG5. It can be seen that replacing one of the four required LAB strains in the four-LAB group with a non-required LAB strain (e.g., *Lactobacillus acidophilus* TYCA06 being replaced with *Lactobacillus acidophilus* gL-6 in this example) not only fails to achieve the aforesaid synergistic effect, but also results in a significant negative impact on the overall GABA production capability.

Moreover, a high concentration of GABA could still be detected in the bacterial suspension prepared from the bacterial powder made from the supernatant of a respective one of the fermented cultures of the single-LAB EG2 to EG5 and four-LAB EG1, in particular the four-LAB EG1 (result not shown).

In summary, *Bifidobacterium breve* CCFM1025, *Lactobacillus acidophilus* TYCA06, *Lactobacillus plantarum* LPL28, *Bifidobacterium longum* subsp. *infantis* BLI-02, and *Lactobacillus salivarius* subsp. *salicinius* AP-32 have an excellent GABA production capability, which can be enhanced when these LAB strains are mixed under a specific ratio range. Hence these strains are expected to be useful for mass production of GABA.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for producing γ-aminobutyric acid (GABA), comprising cultivating a probiotic composition including lactic acid bacterial strains capable of producing GABA in a culture medium containing glutamic acid or a salt thereof,
wherein the lactic acid bacterial strains include *Bifidobacterium breve* CCFM1025 which is deposited at the Guangdong Microbial Culture Collection Center (GDMCC) under an accession number GDMCC 60386, *Lactobacillus acidophilus* TYCA06 which is deposited at the China General Microbiological Culture Collection Center (CGMCC) under an accession number CGMCC 15210, and *Lactobacillus plantarum* LPL28 which is deposited at the CGMCC under an accession number CGMCC 17954.

2. The method as claimed in claim 1, wherein a ratio of a number of *Lactobacillus acidophilus* TYCA06 to that of *Lactobacillus plantarum* LPL28 and to that of *Bifidobacterium breve* CCFM1025 ranges from 1:0.2:0.2 to 1:5:1.

3. The method as claimed in claim 1, wherein a ratio of a number of *Lactobacillus acidophilus* TYCA06 to that of *Lactobacillus plantarum* LPL28 and to that of *Bifidobacterium breve* CCFM1025 is 1:4:2.

4. A fermented culture comprising lactic acid bacterial strains and γ-aminobutyric acid (GABA), which is prepared by a method as claimed in claim 1,
wherein the lactic acid bacterial strains include *Bifidobacterium breve* CCFM1025, *Lactobacillus acidophilus* TYCA06, and *Lactobacillus plantarum* LPL28.

5. A pharmaceutical composition, comprising a fermented culture as claimed in claim 4.

6. A food product, comprising a fermented culture as claimed in claim 4.

7. The pharmaceutical composition as claimed in claim 5, further comprising a pharmaceutically acceptable carrier.

8. A method for producing γ-aminobutyric acid (GABA), comprising cultivating a probiotic composition including lactic acid bacterial strains capable of producing GABA in a culture medium containing glutamic acid or a salt thereof,
wherein the lactic acid bacterial strains include *Lactobacillus acidophilus* TYCA06 which is deposited at the China General Microbiological Culture Collection Center (CGMCC) under an accession number CGMCC 15210, *Lactobacillus plantarum* LPL28 which is deposited at the CGMCC under an accession number CGMCC 17954, *Bifidobacterium longum* subsp. *infantis* BLI-02 which is deposited at the CGMCC under an accession number CGMCC 15212, and *Lactobacillus salivarius* subsp. salicinius AP-32 which is deposited at the China Center for Type Culture Collection (CCTCC) under an accession number CCTCC M 2011127.

9. The method as claimed in claim 8, wherein a ratio of a number of *Lactobacillus acidophilus* TYCA06 to that of *Lactobacillus plantarum* LPL28, to that of *Bifidobacterium longum* subsp. *infantis* BLI-02, and to that of *Lactobacillus salivarius* subsp. salicinius AP-32 ranges from 1:0.067:0.067:0.067 to 1:4:4:4.

10. The method as claimed in claim 9, wherein the ratio of the number of *Lactobacillus acidophilus* TYCA06 to that of *Lactobacillus plantarum* LPL28, to that of *Bifidobacterium longum* subsp. *infantis* BLI-02, and to that of *Lactobacillus salivarius* subsp. salicinius AP-32 is 1:1:1:1.

11. A fermented culture comprising lactic acid bacterial strains and γ-aminobutyric acid (GABA), which is prepared by a method as claimed in claim 8,
wherein the lactic acid bacterial strains include *Lactobacillus acidophilus* TYCA06, *Lactobacillus plantarum* LPL28, *Bifidobacterium longum* subsp. *infantis* BLI-02, and *Lactobacillus salivarius* subsp. salicinius AP-32.

12. A pharmaceutical composition, comprising a fermented culture as claimed in claim 11.

13. The pharmaceutical composition as claimed in claim 12, further comprising a pharmaceutically acceptable carrier.

14. A food product, comprising a fermented culture as claimed in claim 11.

* * * * *